(12) United States Patent
Pianykh et al.

(10) Patent No.: US 8,795,386 B2
(45) Date of Patent: Aug. 5, 2014

(54) BELOW KNEE AMPUTEE PROSTHESIS LINER

(75) Inventors: Oleg Pianykh, Salt Lake City, UT (US); Charles C. Polta, Salt Lake City, UT (US); Kai Bussiek-Cillien, Gottingen (DE); Scott John Schneider, Sartell, MN (US)

(73) Assignee: Otto Bock Healthcare GmbH, Duderstadt (DE)

( * ) Notice: Subject to any disclaimer, the term of this patent is extended or adjusted under 35 U.S.C. 154(b) by 165 days.

(21) Appl. No.: 13/299,532

(22) Filed: Nov. 18, 2011

(65) Prior Publication Data

US 2013/0131831 A1    May 23, 2013

(51) Int. Cl.
    *A61F 2/78*    (2006.01)
    *A61F 2/50*    (2006.01)
    *A61F 5/01*    (2006.01)

(52) U.S. Cl.
    CPC ....... *A61F 2/7812* (2013.01); *A61F 2002/5007* (2013.01); *A61F 2002/7818* (2013.01); *A61F 2002/785* (2013.01); *A61F 2005/0174* (2013.01)
    USPC .......................................................... 623/36

(58) Field of Classification Search
    CPC ........... A61F 2/7812; A61F 2002/7818; A61F 2002/785
    USPC .................................................... 623/36, 37
    See application file for complete search history.

(56) References Cited

U.S. PATENT DOCUMENTS

| | | | |
|---|---|---|---|
| 2,202,598 A * | 5/1940 | Peterson | 623/32 |
| 5,007,937 A * | 4/1991 | Fishman et al. | 623/34 |
| 5,888,216 A | 3/1999 | Haberman | |
| 6,136,039 A | 10/2000 | Kristinsson et al. | |
| 6,149,691 A | 11/2000 | Fay et al. | |
| 6,362,387 B1 * | 3/2002 | Carlson et al. | 602/41 |
| 6,440,345 B1 | 8/2002 | Hellberg | |
| 6,918,936 B2 | 7/2005 | Hellberg | |
| 2005/0240283 A1 | 10/2005 | Kania | |
| 2007/0061017 A1 | 3/2007 | Wilson | |
| 2009/0132056 A1 | 5/2009 | Kania | |
| 2010/0016993 A1 | 1/2010 | Mackenzie | |
| 2010/0076357 A1 | 3/2010 | Schneider | |

(Continued)

FOREIGN PATENT DOCUMENTS

| | | |
|---|---|---|
| EP | 1618858 B1 | 9/2008 |
| SU | 1 739 990 A1 | 6/1992 |
| WO | 2009109182 A1 | 9/2009 |
| WO | 2011062619 A1 | 5/2011 |

OTHER PUBLICATIONS

SU 1739990 A (Jun. 15, 1992): English language translation.*

(Continued)

*Primary Examiner* — David H Willse
(74) *Attorney, Agent, or Firm* — Holland & Hart (57) ABSTRACT

A below knee amputee prosthesis liner including a molded polymer-like liner body for receiving a below knee amputation limb of a person. The liner body has a closed distal end and an open proximal end. The liner includes at least one thickening in a first region and/or in a second region. The first region is adapted to cover a head of the fibula of the amputation limb and the second region is adapted to cover a shinbone of the amputation limb, once the amputation limb is received in the liner body.

19 Claims, 8 Drawing Sheets

(56) References Cited

U.S. PATENT DOCUMENTS

2010/0274363 A1    10/2010    Laghi et al.
2011/0054635 A1    3/2011    Watts
2011/0098827 A1    4/2011    Laghi et al.
2011/0118854 A1    5/2011    Halldorsson

OTHER PUBLICATIONS

PCT International Search Report for PCT International No. PCT/US2012/065888 mailed Mar. 1, 2013 (4 pp.).

* cited by examiner

BELOW KNEE AMPUTEE PROSTHESIS LINER

TECHNICAL FIELD

The present disclosure generally relates to prosthetic devices and in particular to a prosthetic liner for a below knee amputee comprising a molded polymer-like liner body for receiving a below knee amputation limb of a person, the liner body having a closed distal end and an open proximal end. The present disclosure further relates to a method for producing such a liner.

BACKGROUND

The use of prosthetic liners for below knee amputees is well known from the prior art. A prosthetic liner is worn between the amputation limb and the prosthesis socket, carrying the lower leg portion of the prosthesis. The liner is worn directly on the amputation limb. At the closed distal end of the liner body the liner is provided with means for connecting the liner to the prosthesis socket. These means might, for example, be threaded inserts, which may be molded into the polymer-like liner material, in particular by injection molding.

Since the liner usually is the only part of the prosthesis getting in direct contact with the skin of the amputee and the liner is usually worn the whole day, it is important to make the liner as comfortable to wear as possible. The liners might be, for example, constructed either of a fabric impregnated with silicone or another polymer-like material or from the polymer-like material only.

From U.S. Pat. Nos. 6,440,345 B1 and 6,918,936 B2 a liner is known, which comprises a knee part having a pre-flexed angle. This is also known from U.S. Pat. No. 5,888,216. Compared with the straight tubular shape liner, this pre-flexed angle minimizes the wrinkling behind the knee, especially when the knee is bent. In addition it increases the range of motion of the knee joint and is more comfortable to wear when sitting.

Since the diameter of the amputation limb of the person usually decreases towards the distal end of the amputation limb, the distal part of the liner according to U.S. Pat. No. 5,888,216 is tapered. This leads to a better fit and a more homogeneous distribution of pressure at the amputation limb of the person.

From US 2010/0016993 a liner is known, which also shows a knee part, in which a strip or a tendon is attached to urge the elastomeric material in this region of the tubular liner body to contract. This strip or tendon is, for example, of silicone having a higher durometer hardness value than the material of the liner body and may be, for example, integrally molded with the knee portion of the tubular liner body.

In order to provide a perfect fit of the liner at the residual limb of the person it is possible to use a fully individualized liner or to individualize a standard liner, as, for example, is known from WO 2009/109182. Since the construction of an individual liner is time-consuming and expensive it is much cheaper and faster to provide some standard liners which may be available in different sizes and to use these standard liners for each amputation limb.

Unfortunately, amputation limbs are shaped very individually. When a standard liner is used it is possible that cavities occur between the amputation limb of the person and the liner. This may lead to swelling or chafing at the residual limb. In order to prevent at least most of these cavities from occurring between the liner and the residual limb it is known, for example, from US 2005/0240283 A1 to insert some cushions into the liner. This leads to a more homogeneous distribution of pressure at the surface of the amputation limb covered by the liner.

At the distal end of the liner there is usually a means for connecting the liner to the remaining parts of the prosthesis. Silicone liners particularly utilize a hard unyielding material such as aluminum or thermoplastics such as polycarbonate or polyamids as a shuttle screw housing for fixing the lower leg portion of the prosthesis. The said means may also be a screw housing or a threaded insert which might be molded into the material of the liner body. In order to prevent these hard materials from being felt by the wearer of the prosthesis liner, the thickness of the molded polymer-like liner material is considerably enhanced at the closed distal end of the liner body.

In order to increase the wearing comfort of the prosthesis even further, it is known to insert some cushions into the prosthetic socket, which is to be fixed to the liner. Since the prosthetic socket is made from a rigid material, this may lead to bruising and chafing and hence to discomfort and pain.

These cushions are usually positioned at an inner surface of the prosthetic socket. This leads to dirt pockets making the cleaning of the prosthetic socket difficult and time-consuming. In addition it is difficult to position these cushions at the inner surface of the prosthesis socket exactly. This might lead to wrong positions of the cushions so that the desired cushioning effect is not realized or at least is not realized at the desired locations at the amputation limb. This again leads to chafing, pressure points, swelling and pain.

SUMMARY

An object of the present disclosure is to provide a liner for a below knee amputee prosthesis, which increases the wearing comfort of the prosthetic device and makes the prosthetic socket to be attached to the liner easier to clean.

Another object of the present disclosure is to provide a method for producing such a liner.

In one example, a below knee amputee prosthetic liner comprises a molded polymer-like liner body for receiving a below knee amputation limb of a person, the liner body having a closed distal end and an open proximal end, wherein the liner comprises at least one thickening in at least one of a first region and a second region, the first region being adapted to cover a head of the fibula of the amputation limb and the second region being adapted to cover a shinbone of the amputation limb, once the amputation limb is received in the liner body.

The at least one thickening provides a cushioning effect for the head of at least one of the fibula and the shinbone of the amputation limb. Because of this additional cushioning of the prominent bones of the amputation limb the liner is very comfortable to wear. In addition, there are no more cushions to be provided at an inner surface of a prosthetic socket, which is to be attached to the prosthesis liner. Hence, the inner surface of a prosthetic socket may be flat and smooth making it is easier to clean.

In one embodiment the liner is symmetric with respect to a plane of symmetry in which the knee of the amputation limb is bendable, once the amputation limb is received in the liner body. The plane of symmetry is the so called sagittal plane. By this it is possible to use the same liner for a below knee amputation limb of a right leg and of a left leg. The liner hence has two thickenings for covering the head of the fibula, one of which is provided on the right hand side of the liner body and the other one is provided is one the left hand side, i.e. on the medial and lateral sides.

The at least one thickening may be formed by at least one pad arranged at the liner body. These pads may be prefabricated making it easier to produce a liner according to the present disclosure. The pad and the liner body may either be made from the same material, such as polyurethane or silicone or any other suitable polymer-like material, or from different materials. In this case it is possible to use materials with different shore hardnesses.

In one embodiment the liner body is molded to the at least one pad or the at least one pad is, for example, glued to the liner body.

In one embodiment, the liner body comprises a knee portion having a pre-flexed angle. By this it is easily possible to determine which part of the liner body is intended to cover the head of the fibula and which part is intended to cover the shinbone. This is possible, because the position of the knee is predetermined to be in the knee portion. In addition, it is very easy to put on the liner in a reproducible manner such that it is ensured that the thickenings are arranged at their proper positions.

An example method for producing a liner according to the present disclosure comprises the step of forming at least one thickening in at least one of the first region and the second region. This forming may comprise the steps of positioning at least one prefabricated pad at a mold core, applying a layer of liner body material, and hardening of the liner body material.

The step of applying the layer of liner body material may include immersing the mold core and the positioned pads into the liner body material. Alternatively the applying of the layer of liner body material includes injection molding, casting or dipping of the liner body material.

In another embodiment of the method, the forming the at least one thickening includes the step of applying at least one prefabricated pad onto an outer surface of the liner body. This may be done, for example, by gluing the pad on the surface of the liner body. Alternatively, the at least one thickening is integrally formed with the liner body, in particular by injection molding.

BRIEF DESCRIPTION OF THE DRAWINGS

FIG. 7 shows another sectional view of a liner according to a further embodiment of the present disclosure with pads on the outside of the liner body.

DETAILED DESCRIPTION

Figure 1:
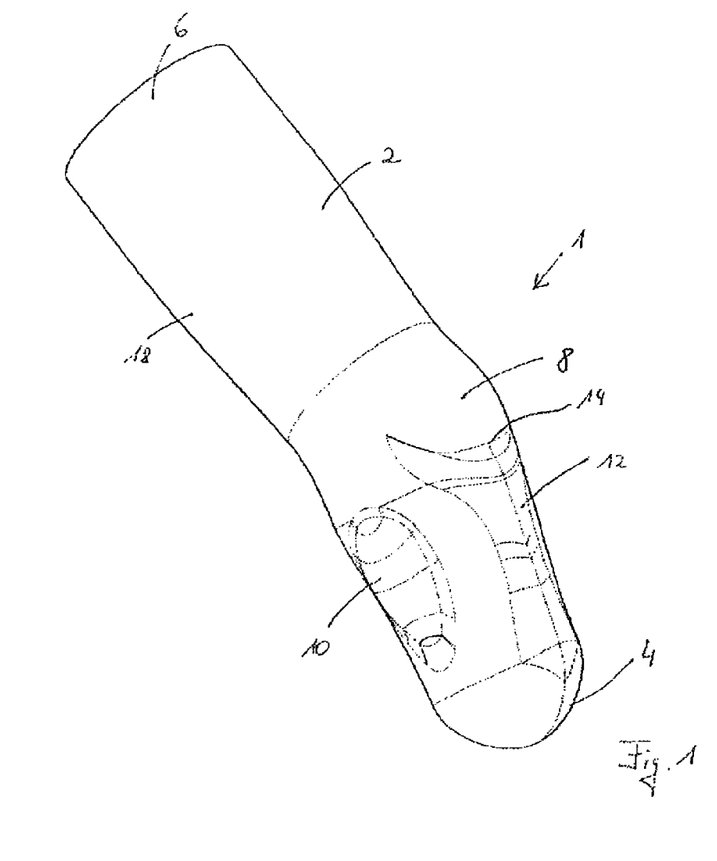
FIG. 1 is a schematic three-dimensional view of a below knee amputee prosthetic liner according to one embodiment of the present disclosure.

FIG. 1 shows a three-dimensional view of a liner 1 according to a first embodiment of the present disclosure. It shows a liner body 2 having a closed distal end 4 and an open proximal end 6. The proximal end 6 is adapted to receive an amputation limb of a person. The liner body 2 comprises a knee part 8 having a pre-flexed angle.

The liner 1 according to the embodiment shown in FIG. 1 has a first thickening 10 in a first region of the liner body 2. The first region is intended to cover the head of the fibula of the person. The first thickening 10, which is in FIG. 1 a prefabricated pad connected to the liner body 2, for example, by one of the previously mentioned methods, cushions the head of the fibula when the amputation limb is received in the liner 1 and the liner 1 is worn by the amputee.

In addition, the liner 1 shown in FIG. 1 has a second thickening 12, which is positioned in a second region of the liner 1. This second thickening 12 is intended to cover the shinbone of the amputation limb when the liner 1 is worn by the amputee. Determining the first and second regions of the liner 1 as well as positioning the first thickening 10 and the second thickening 12 is easily possible, since the position of the knee is determined by the knee part 8 and in particular by the pre-flexed angle.

As may be seen in FIG. 1, the second thickening 12 has a curved upper edge 14 which is adapted to follow the shape of a patella of the amputation limb. This leads to an optimally positioned second thickening 12 and an optimal protection of the shinbone without affecting the patella.

Figure 2:
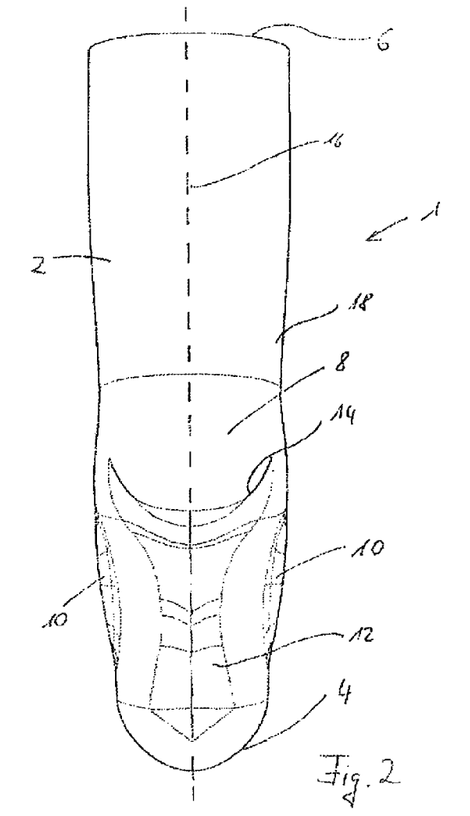
FIG. 2 is a schematic three-dimensional view of the liner of FIG. 1 from another point of view.
Figure 3:
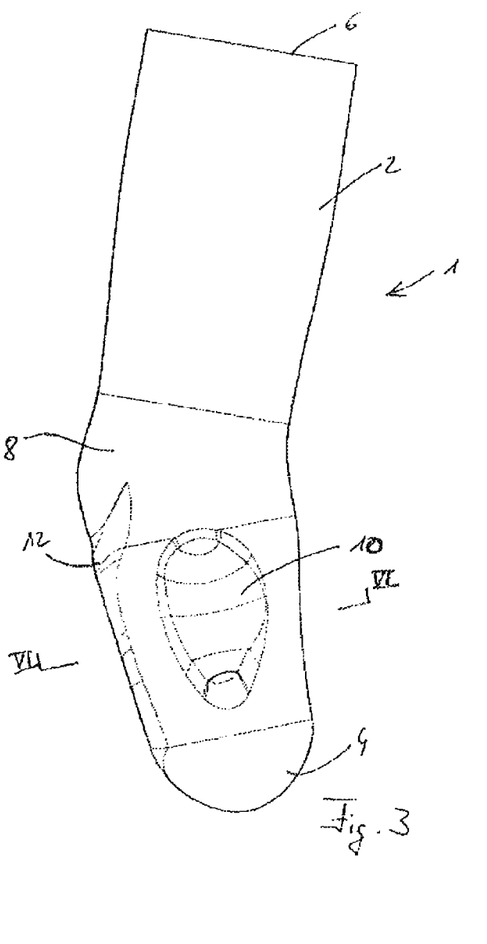
FIG. 3 is a schematic three-dimensional view of the liner of FIGS. 1 and 2 from a third point of view.

FIG. 2 shows the liner 1 of FIG. 1 from another point of view. From FIG. 2 it becomes clear that the liner 1 has two first thickenings 10, one of which is positioned on the right hand side of the second thickening 12 and the other one is positioned on the left hand side of the second thickening 12. It is therefore possible to use the liner 1 for both an amputation limb of a right leg and a left leg. The dashed line in FIG. 2 indicates a plane of symmetry 16 with respect to which the liner 1 is symmetric. FIG. 3 shows a side view of the liner 1. The first thickenings 10 are positioned on the lateral and medial side of the liner 1.

Figure 4:
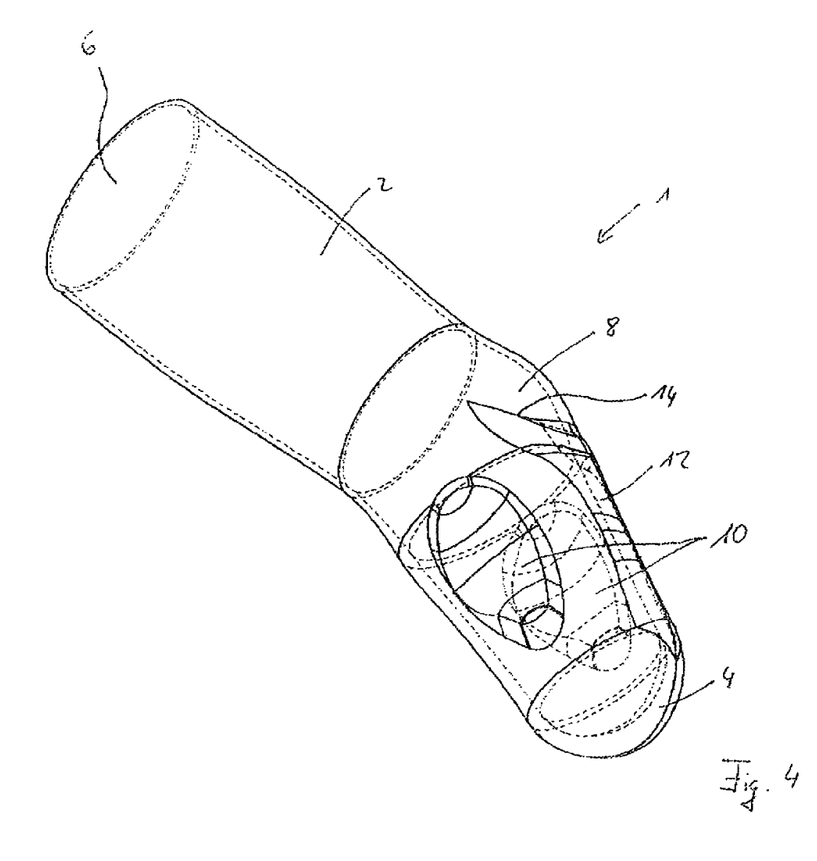
FIG. 4 is another schematic three-dimensional view of a liner according to a second embodiment of the present disclosure.

FIG. 4 shows another three-dimensional view of the liner 1. The parts that are not visible from this point of view are shown in dashed lines. Again two first thickenings 10 are shown. Between these first thickenings 10 a second thickening 12 with the curved upper edge is positioned. The thickness of the liner body 2 varies along the liner body 2. It is smallest at the open proximal end 6 and increases towards the closed distal end. By this the high pressures in this area when a person wears the liner 1 and walks with a prosthesis are cushioned to make the prosthesis more comfortable to wear.

Figure 5:
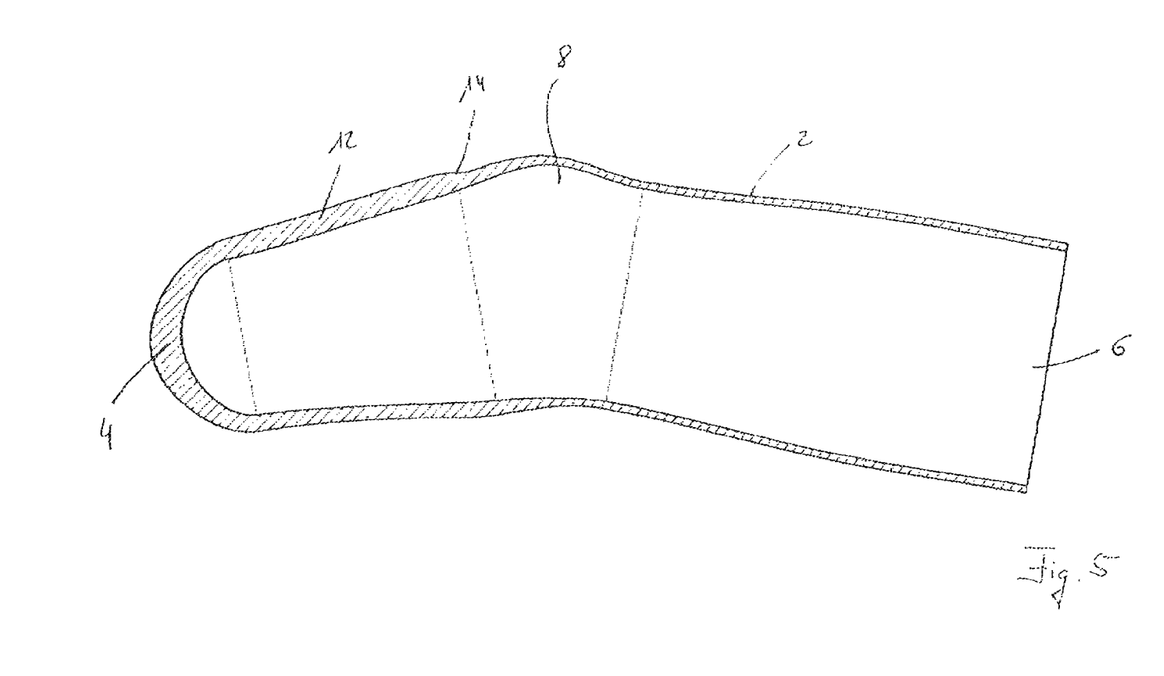
FIG. 5 shows a first sectional view of a liner according to a further embodiment of the present disclosure.

FIG. 5 shows a sectional view along the paper direction in FIG. 3. From this view it becomes clear that the thickness of the liner body decreases from the closed distal end 4 towards the open proximal end 6. Furthermore, the second thickening 12 in the second region of the liner body 2 and the curved upper edge of this thickening 12 is depicted.

Figure 6:
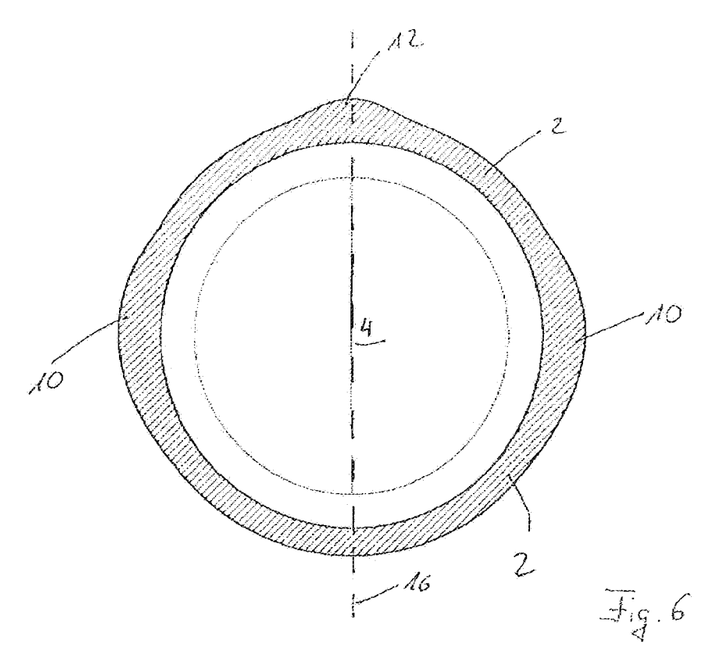
FIG. 6 shows another sectional view of the liner according to a further embodiment of the present disclosure.

FIG. 6 shows a sectional view along the line VI-VI in FIG. 3. One may clearly distinguish the two first thickenings 10 and the second thickening 12. The dashed line again denotes the plane of symmetry 16.

In FIG. 5 and FIG. 6 the liner body 2 is shown with integrally formed first thickening 10 and second thickening 12. This may, for example, be achieved by molding. Alternatively it is possible to use prefabricated pads for creating the first thickening 10 and the second thickening 12. This is, for example, shown in FIG. 1 to FIG. 4, in which the pads are glued on an outer surface 18 of the liner body 2.

FIG. 7 shows a sectional view again along the line VI-VI in FIG. 3. It thus shows the same view as FIG. 6. In contrast to the liner according to FIG. 6 the two first thickenings 10 and the second thickening 12 are not integrally formed with the liner body 2, but consist of three pads 20, which in the embodiment according to FIG. 7 are glued on the outer surface 18 of the liner body 2.

Alternatively, the pads 20 may be arranged at an inner surface 22 of the liner body 2. To position the pads 20 at the inner surface 22 the pads 20 are arranged at a mold core in a first step. The mold core represents the amputation limb that is to be covered by the liner 1. After this, at least one layer of liner body material is applied to the mold core, for example by immersing the mold core and the pads 20 into a bath of this material. Alternatively, the liner body material may be molded or filled into a form, in which the mold core and the pads 20 are arranged.

Figure 8:
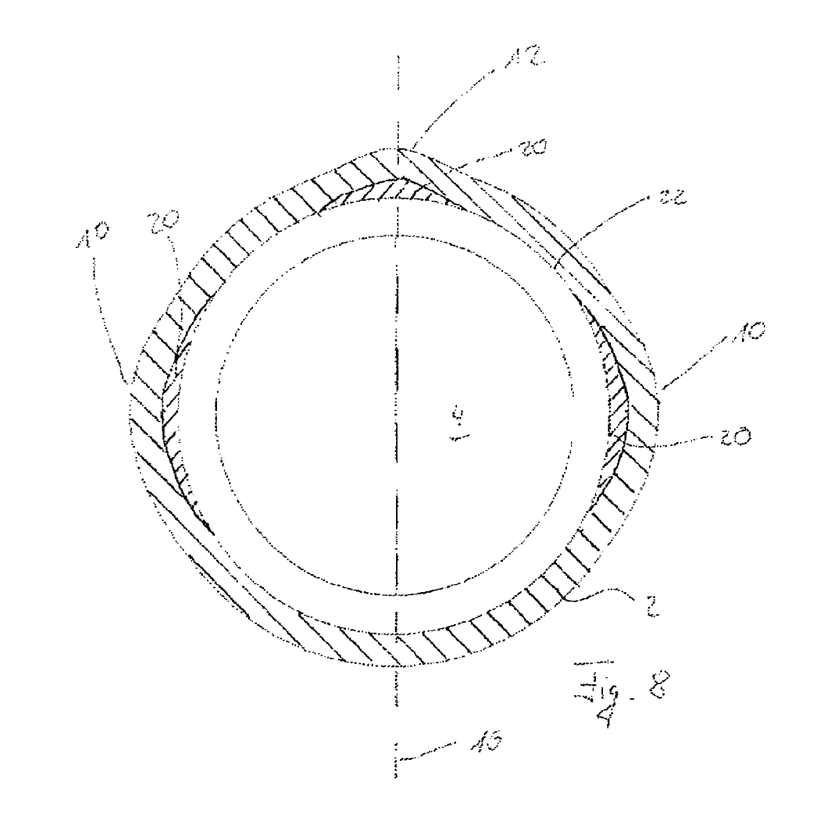
FIG. 8 shows a sectional view of the liner according to a further embodiment of the present disclosure with pads on the inside of the liner body.

This situation is shown in FIG. 8, which again shows a sectional view along the line VI-VI in FIG. 3. The pads 20 are arranged at the inner surface 22 of the liner body 2.

We claim:

1. A below knee amputee prosthetic liner, comprising:
   a molded polymer-like liner body for receiving a below knee amputation limb of a person, the liner body having a closed distal end and an open proximal end;
   wherein the liner comprises first and second thickenings in a first region and at least one third thickening in a second region, the first region being adapted to cover a medial and a lateral side of a head of the fibula of the amputation limb with the first thickening being positioned on the medial side of the head of the fibula and the second thickening being positioned on the lateral side of the head of the fibula, and the second region being adapted to cover a shinbone of the amputation limb, once the amputation limb is received in the liner body;
   wherein the liner is symmetric with respect to a sagittal plane.

2. The liner of claim 1, wherein the first, second and third thickenings are formed by at least one pad arranged at the liner body.

3. The liner of claim 2, wherein the pad and the liner body are made from the same material, in particular from polyurethane or silicone.

4. The liner of claim 2, wherein the pad and the liner body are made from different materials.

5. The liner of claim 2, wherein the liner body is molded to the at least one pad, in particular by injection molding, by casting or by dipping.

6. The liner of claim 2, wherein the at least one pad is glued to the liner body.

7. The liner of claim 1, wherein the liner body comprises a knee portion having a pre-flexed angle.

8. A method for producing a liner, comprising:
   providing a molded polymer-like liner body for receiving a below knee amputation limb of a person, the liner body having a closed distal end and an open proximal end;
   forming first and second thickenings in a first region and at least one third thickening in a second region, the first region being adapted to cover a medial and a lateral side of a head of a fibula of the amputation limb with the first thickening being positioned on the medial side of the head of the fibula and the second thickening being positioned on the lateral side of the head of the fibula, and the second region being adapted to cover a shinbone of the amputation limb, once the amputation limb is received in the liner body;
   wherein the liner is symmetric with respect to a sagittal plane.

9. The method of claim 8, wherein the forming of the first, second and third thickenings comprises:
   positioning at least one prefabricated pad at a mold core;
   applying at least one layer of a liner body material;
   hardening of the liner body material.

10. The method of claim 9, wherein the step of applying the layer of liner body material includes immersing the mold core and the positioned pad into the liner body material.

11. The method of claim 9, wherein the step of applying the layer of liner body material includes injection molding of the liner body material.

12. The method of claim 8, wherein forming the first, second and third thickenings includes applying at least one prefabricated pad onto an outer surface of the liner body.

13. The method of claim 8, wherein the first, second and third thickenings are integrally formed with the liner body, in particular by injection molding.

14. A below knee amputee prosthetic liner, comprising:
   a molded polymer-like liner body configured to receive a below knee amputation limb and being symmetric with respect to a sagittal plane, the liner body comprising:
   a closed distal end;
   an open proximal end;
   first and second thickenings positioned in a first region of the liner body;
   at least one third thickening positioned in a second region of the liner body;
   wherein the first region is configured to cover a medial and a lateral side of a head of the fibula of the amputation limb with the first thickening being positioned on the medial side of the head of the fibula and the second thickening being positioned on the lateral side of the head of the fibula, and the second region is configured to cover a shinbone of the amputation limb, once the amputation limb is received in the liner body.

15. The liner of claim 14, wherein the first, second and third thickenings are formed by at least one pad arranged at the liner body.

16. The liner of claim 15, wherein the pad and the liner body are made from the same material, in particular from polyurethane or silicone.

17. The liner of claim 15, wherein the pad and the liner body are made from different materials.

18. The liner of claim 15, wherein the liner body is molded to the at least one pad, in particular by injection molding, by casting or by dipping.

19. The liner of claim 15, wherein the at least one pad is glued to the liner body.

* * * * *